United States Patent [19]

Baker, Jr. et al.

[11] Patent Number: 4,880,004

[45] Date of Patent: Nov. 14, 1989

[54] IMPLANTABLE CARDIAC STIMULATOR WITH AUTOMATIC GAIN CONTROL AND BANDPASS FILTERING IN FEEDBACK LOOP

[75] Inventors: Ross G. Baker, Jr.; Richard V. Calfee, both of Houston; Edward A. Haluska, Angleton; Stephen J. Whistler, Lake Jackson, all of Tex.

[73] Assignee: Intermedics, Inc., Angleton, Tex.

[21] Appl. No.: 203,322

[22] Filed: Jun. 7, 1988

[51] Int. Cl.[4] .................. A61N 1/00; H05G 00/00
[52] U.S. Cl. ............................... 128/419 PG
[58] Field of Search ......... 128/419 D, 419 P, 419 PG

[56] References Cited

U.S. PATENT DOCUMENTS

| | | | |
|---|---|---|---|
| 4,406,287 | 9/1983 | Nappholz et al. | 128/419 PG |
| 4,523,595 | 6/1985 | Zibell | 128/419 D |
| 4,554,921 | 11/1985 | Boute et al. | 128/419 PG |
| 4,766,902 | 8/1988 | Schroeppel | 128/419 PG |
| 4,768,511 | 9/1988 | DeCote, Jr. | 128/419 PG |
| 4,774,950 | 10/1988 | Cohen | 128/419 D |

Primary Examiner—Francis Jaworski
Assistant Examiner—George Manuel
Attorney, Agent, or Firm—John R. Merkling

[57] ABSTRACT

An implantable cardiac stimulator for detecting and treating cardiac arrhythmias includes a sense amplifier responsive to sensed cardiac signals for detecting and distinguishing normal and abnormal cardiac activity within the sensed signals. The sense amplifier includes an automatic gain control amplifier, a filter and quad comparator having a pair of signal channels for processing the sensed signals according to different frequency bandpass characteristics to establish sensing thresholds, margins and signal gain. The sense amplifier has a feedback loop containing a microprocessor which implements preselected algorithms in conjunction with the outputs of the quad comparator to variably adjust the amplifier gain and to programmably control the sensing margin.

34 Claims, 5 Drawing Sheets

AGC AMPLIFIER SECTION

FIG. 4
BANDPASS AMPLIFIER SECTION

FIG. 5

QUAD COMPARATOR SECTION

IMPLANTABLE CARDIAC STIMULATOR WITH AUTOMATIC GAIN CONTROL AND BANDPASS FILTERING IN FEEDBACK LOOP

CROSS-REFERENCE TO RELATED APPLICATION

This application is related to the subject matter of copending U.S. patent application Ser. No. 875,218 titled "IMPLANTABLE CARDIAC STIMULATOR FOR DETECTION AND TREATMENT OF VENTRICULAR ARRHYTHMIAS," filed June 17, 1986, assigned to the same assignee as is the present application.

FIELD OF THE INVENTION

The present invention relates generally to implantable cardiac stimulators such as pacemakers and defibrillators or combinations thereof, and more particularly to automatic gain control for such implantable devices for the purpose of enhancing the capability of the device to sense an arrhythmia for which therapy is to be applied.

BACKGROUND OF THE INVENTION

Arrhythmias are variations in heart rate from the normal sinus rate range of approximately 60 to 120 beats per minute (bpm) prevalent in healthy adult humans with normally functioning hearts. Bradycardia is characterized by rates below 60 bpm, whereas for tachycardia the rates generally range upwardly from 120 bpm. Typically, tachycardia is experienced as a result of such factors as physical stress (exercise), emotional stress (excitement), consumption of alcoholic or caffeinated beverages, ingestion of certain drugs such as nicotine, and so forth. The heart rate of a healthy person will gradually return to the sinus rate after removal of the tachycardia-inducing factor(s). However, arrhythmias require special medical treatment. For example, fibrillation is a high rate arrhythmia tachyarrhythmia characterized by completely uncoordinated contractions of sections of conductive cardiac tissue of the affected chamber of the heart, resulting in a complete loss of synchronous contraction of the overall mass of tissue. As a consequence, the chamber ceases to pump blood effectively and, in the case of ventricular fibrillation, the lack of oxygenated blood to the tissues will lead to death within minutes.

Implantation of a cardiac pacemaker has been a typical procedure of choice for treatment of bradycardia patients. The pacemaker pulse generator is implanted in a pouch beneath the skin in the patient's chest and delivers electrical impulses to electrodes positioned at the patient's heart via one or more catheter leads, to stimulate the heart to beat at a desired rate in the normal sinus range. Cardiac pacing has also found increasing usage in the management of tachyarrhythmia. In essence, the heart may be artificially stimulated at a faster than normal pacing rate to terminate a tachycardia or to suppress premature atrial or ventricular contractions which could otherwise lead to supra-ventricular or ventricular tachycardia, flutter, or fibrillation. The pulses delivered to the heart for pacing therapy need only be of sufficient magnitude to stimulate the excitable myocardial tissue in the immediate vicinity of the pacing electrode.

More recently, the automatic defibrillator has been proposed for implantation in cardiac patients prone to suffer ventricular tachycardia and/or fibrillation. The device is adapted to shock the heart with electrical pulses of considerably higher energy content than is delivered in pacing pulses. Upon detecting fibrillation, one or more high energy "counter-shocks" are applied to the heart to overwhelm the chaotic contractions of individual tissue sections and re-establish organized spreading of action potential from cell to cell of the myocardium, thereby restoring the synchronized contraction of the mass of tissue. In general, prior art implantable defibrillators have been implemented to detect fibrillation from the patient's electrogram waveform and/or the absence of a "mechanical" function such as rhythmic contractions or pulsatile arterial pressure, and, in response, to deliver a fixed therapy typically consisting of one or more shocking pulses of preset waveform and energy content.

For example, detection of fibrillation activity by monitoring the electrogram signal has been achieved with conventional sense amplifier configurations involving fixed sense margin, fixed or selectively adjusted gain and fixed bandpass characteristics. This type of detection tends to neglect the characteristic differences between QRS complexes and fibrillation waveforms. Fibrillation waveforms are characterized by erratic amplitude modulated sinusoids of relatively low frequency in a narrow band (3–12 Hz). On the other hand, QRS complexes have relatively constant amplitude, sharp peaks with significant high frequency content and thus a broader frequency spectrum.

The aforementioned co-pending U.S. patent application Ser. No. 875,218 discloses an improved medical device for treating ventricular tachycardia and defibrillation, which uses sophisticated techniques for detecting and distinguishing the arrhythmia from normal high rates, and a hierarchical approach to the aggressiveness and delivery of therapies to terminate the arrhythmia. The functions of bradycardia and anti-tachycardia pacing-type therapies, and cardioversion and debifrillation shock-type therapies, are integrated to provide a coordinated approach to the management and treatment of ventricular arrhythmias. A significant aspect of that approach is to provide flexible sequencing among the therapies, with appropriate regard to hemodynamic tolerance (or intolerance) of the patient to the detected arrhythmia, and sophisticated detection of arrhythmias together with means for distinguishing those episodes for which treatment is required (such as re-entrant tachycardias) from those which are not associated with cardiac or other disease (such as exercise-generated sinus tachycardias). A multiplicity of hierarchical detection algorithms and therapeutic modalities are selectively available to the physician to detect and treat classes of ventricular tachycardia according to their respective positions in the heart rate continuum, and thus according to hemodynamic tolerance or intolerance of the patient to the tachycardia, with backup capabilities of defibrillation and bradycardia pacing for cardiac arrhythmias, including postshock bradycardia.

In an embodiment described in the 875,218 application, the cardiac stimulator permits selective partitioning of the heart rate continuum into a plurality of contiguous tachycardia classes of progressively higher rate ranges, the lowest and highest of these classes being bounded respectively by regions of the continuum denoting sinus rate and fibrillation. Each of the rate ranges and the latter regions may be programmed by the physician, as may be necessary to meet the particular needs of the patient's disorder and the flexibility of the therapy regimens to be prescribed. The hierarchical detection system employed in the stimulator for detecting cardiac episodes indicative of arrhythmia and for distinguishing between normal and abnormal tachycardias among the detected episodes uses criteria of greater or lesser stringency depending on the location of the episode in the rate continuum. The device permits programming of the various detection criteria for tachycardias and fibrillation, and includes plural combinations of basic detection criteria in each category. The arrhythmia detection system disclosed in that application also utilized signal processing including amplification with automatic gain control and bandpass filtering according to the present invention, for enhancing sensitivity to the differences between the electrical and physical characteristics of sinus rhythms and arrhythmia waveforms.

It should be noted that the prior art has suggested the analysis of waveform morphology for fibrillation detection. Moreover, it is known to use automatic gain control in defibrillation systems. A principal object of the present invention, however, is the provision of a system and method for arrhythmia detection which recognizes and takes advantage of the characteristic differences between sinus rhythm and arrhythmias, including those mentioned above, utilizing automatic gain control and bandpass filtering in a feedback loop.

Another significant object of the present invention is to provide an implantable cardiac stimulator utilizing automatic gain control in interaction with arrhythmia detection, as well as with special bandpass characteristics and bradycardia pacing.

A further important object of the present invention is to provide an approach for dealing with interactions between gain and pacing in an implantable device capable of treating bradyarrhythmias as well as tachyrhythmias.

Yet another object of the invention is to provide an implantable device which implements the foregoing objectives in treating tachycardia and fibrillation, and which is adapted also to treat post-shock bradycardia.

Still another object of the present invention is to provide a cardiac arrhythmia detection system and method employing automatic gain control in conjunction with bandpass filtering in a feedback loop, wherein the margin of sensitivity to the various waveforms encountered varies to enhance the capability and speed of detection of the arrhythmias of interest, such that an appropriate therapy is quickly applied to return the heart to normal sinus rhythm.

SUMMARY OF THE INVENTION

According to the present invention, the sense amplifier of the cardiac stimulator is provided with automatic gain control (AGC) as well as bandpass filtering and comparison of sensed signal (sensed event) amplitudes against selected target levels in a system and method for detecting cardiac arrhythmias. Interactions between gain, bandpass and pacing are utilized in a manner not found in prior art techniques employed to detect and treat cardiac arrhythmias. In essence, the invention addresses bandpass filtering and its effect on sensing margins; varies the sensing margin with the shape of the waveform under analysis; minimizes noise and T wave sensing while QRS complexes are present; and maximizes sensing of fibrillation waveforms in the face of widely varying amplitudes.

The AGC amplifier includes an amplifier section having a gain that may be altered as often as necessary to maintain a set of predefined conditions, a set of bandpass amplifiers with different characteristics for AGC and sense target comparators, and a dual set of comparators to convert the processed analog information into digital information to be used by a microprocessor for making decisions about the need for changes in the gain of the amplifier and sensing activity.

The present invention takes advantage of the differences between waveforms or signals representative of cardiac arrhythmias and those indicative of normal sinus rhythm to provide rapid detection. For example, differences in the characteristics of fibrillation waveforms and standard QRS complexes include wide and frequent variation in the amplitude of a fibrillation. It set to a gain to assure sensing over the necessarily wide amplitude range of interest (e.g., 0.3 mv to tens of millivolts), the device could sense and respond to false signals including the unwanted noise signals which are often present in the absence of fibrillation at typically low amplitude levels (e.g. T-waves).

Accordingly, it is a more specific object of the invention to provide a fibrillation detection method and system for a cardiac stimulator capable of automatic delivery of defibrillating therapy, in which signal amplification with automatic gain control and bandpass filtering is utilized for reliably sensing wide and frequent amplitude variation of fibrillation waveforms.

Another significant object of the present invention is to provide automatic gain control in the signal analysis path for fibrillation detection, to avoid falsely sensing noise signals as fibrillation and consequent undesirable delivery of unnecessary defibrillating shocks to the patient.

An important aspect of the invention is a set of bandpass amplifiers that produce different bandpass characteristics between peak and sensing comparator targets. Without the differential bandpass characteristic, the sensing margin would be the same for all electrogram waveforms, regardless of their frequency content. In such a system there is a difficult tradeoff between the large sensing margin that would achieve reliable sensing of erratic fibrillation waveforms and a small sensing margin that would sense QRS complexes but reject T-waves. With the addition of the differential bandpass characteristic, fibrillation waveforms (which do not contain the higher frequency components that are characteristic of QRS complexes) are selectively enhanced at the sensing target. This selective enhancement provides the higher sensing margin required to reliably sense this erratic signal. But by not enhancing the higher frequency signal components of QRS complexes, the lower margin needed to reject T-waves is still obtained.

BRIEF DESCRIPTION OF THE DRAWINGS

The above and still further objects, features and attendant advantages of the present invention will become apparent from a consideration of the following detailed description of a presently preferred embodiment, taken in conjunction with the accompanying drawings, in which.

DETAILED DESCRIPTION OF THE PRESENTLY PREFERRED EMBODIMENT

The invention herein will be described in the environment of an implantable cardiac stimulator of the type disclosed in the 875,218 application, but it is not limited to that usage and it will be understood as this description progresses that the invention may be utilized as well in more restricted anti-tachycardia pacemakers or bradycardia pacemakers. While only a portion of the description and drawings of the 875,218 application are repeated in the present application, it is to be understood that the entirety of that co-pending application is incorporated into the present disclosure by reference.

The therapy generator (FIG. 1) unit of the stimulator (akin to the pulse generator unit of an implantable pacemaker) is adapted to detect preselected aspects of the patient's cardiac activity, and to respond to arrhythmias by generating and managing the delivery of pacing and shock therapies. It will be evident, then, that despite its name the therapy generator does more than simply generate therapies, just as the pulse generator of a pacer does more than simply generate pulses; and in particular that the generator incorporates circuitry for sensing cardiac activity. Among other things, the generator has a self-contained power source, and is assembled and housed in a metal case which is inert to body tissue and fluids. Lead/electrode assemblies for use in sensing cardiac activity and delivering the respective pacing and shock impulses to the patient's heart are separably connectable to the therapy generator, in a manner analogous to leads of a cardiac pacemaker. Together, then, the therapy generator and the lead/electrode assemblies constitute the cardiac stimulator.

The therapy generator includes a digital control section for storing and executing software instructions and for storing and processing the data for all digital functions of the device (aside from those functions which, for purposes of conserving memory capacity, are readily consigned to an external programmer unit). Digital functions of the device may include the physician-programmable aspects, such as provision for programming rate boundaries to selectively partition the rate continuum, desired therapy structures and delivery sequences, and detection and redetection algorithms; and, as well, the various processing, timing, switching, control and other functions, all of which are described in detail in the 875,218 application and many of which need not be repeated here inasmuch as they are not essential to an understanding of the present invention.

The therapy generator also includes an analog system portion for functions including those of the present invention involving monitoring of the patient's ECG signal information over each cardiac cycle and enhancing that signal information while reducing noise and other interference through signal filtering and automatic gain control. Other analog functions of the generator include developing the respective impulse waveforms to be delivered for the pacing and shock therapies, transmitting data between the device and external units such as the programmer and transtelephonic monitoring equipment, and protecting against overloads. Also included are the battery cells, and voltage regulation and priority power sequencing section, for supplying power to the other sections of the overall generator.

Figure 1:
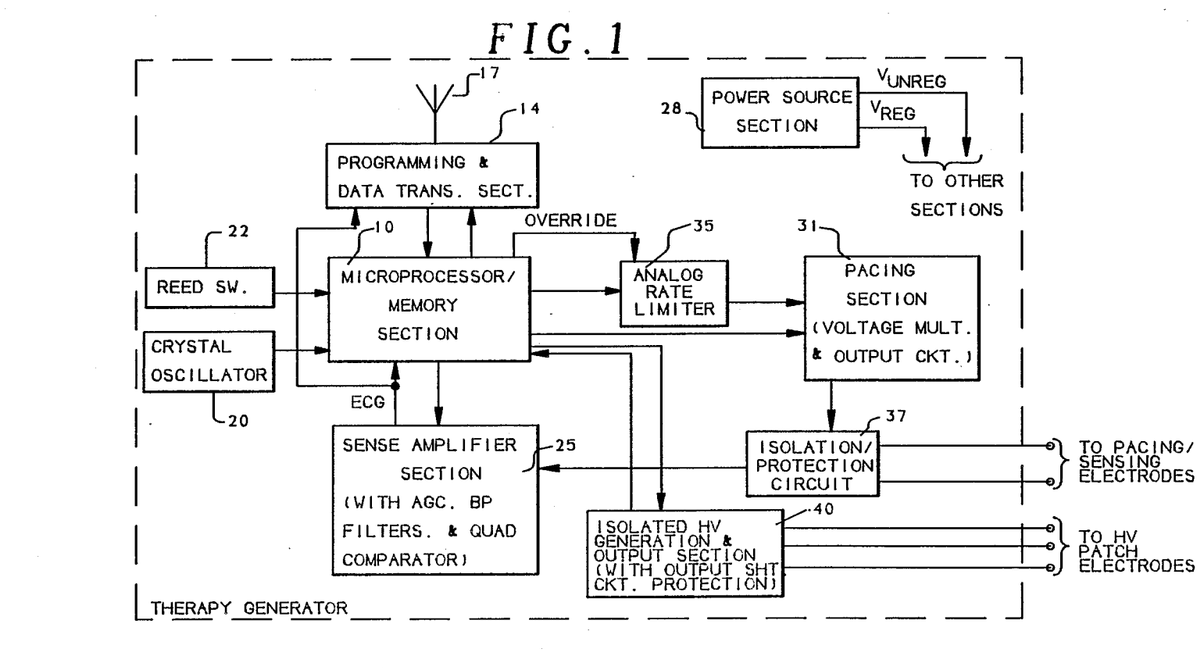
FIG. 1 is a block circuit diagram of the therapy generator of an implantable cardiac stimulator, utilizing a sense amplifier having AGC, bandpass filters and quad comparators according to the presently preferred embodiment.

With reference now to FIG. 1, a central microprocessor and associated memory section 10 of the therapy generator processes and stores the data for rate boundaries within the heart rate continuum, therapy structures, detection algorithms, and other features. Bidirectionally coupled to microprocessor/memory section 10 is a programming and data transmission section 14 for transmitting data to and from the external programmer and/or to receiving and monitoring equipment, via the antenna 17. A crystal oscillator 20 is electrically coupled to section 10 to provide precise timing signals for system operation. A reed switch 22 allows limited external control by the patient of physician-selected programmable functions, by means of placing an external magnet (not shown) in proximity to the switch for actuation thereof.

A sense amplifier section 25 of the present invention, described in detail below, is coupled to the microprocessor/memory section 10 to furnish electrogram signal information and to receive control signals from the microprocessor. The sense amplifier also supplies electrogram signal information directly to data transmission section 14 for telemetry to the external monitoring equipment. A quad comparator within sense amplifier 25 serves as the link to convert electrogram, sense signal information from sensing electrode(s) (not shown) attached to the patient's heart into digital information for use by the microprocessor. The microprocessor 10 is disposed in the feedback loop of the sense amplifier 25 for automatic gain control.

The sense amplifier 25 enhances the electrogram signals to enable tracking the rapidly varying amplitude, of fibrillation signals. Preferably, the sense amplifier 25 has a range of gain of the order of 30:1. As will be explained in more detail below, AGC with bandpass filtering is employed to provide the dual function of reducing the amplitude of signals outside the frequency band of interest, and further amplifying the relatively low frequency (e.g., fibrillation) signals in the absence of normal R-waves.

The power source section 28 of the therapy generator includes high rate battery cells, a voltage regulator and a priority power sequencer none of which are shown and all of which are conventional. The cells are capable of delivering sufficient energy to charge capacitors (not shown) in the output high voltage section 40 within a period of 20 seconds or less. The voltage regulator circuit provides voltage reduction (division) depending on the number and connection of cells employed, to improve power source efficiency. The priority power sequencer assures that adequate power is made available to essential circuit functions, including the control logic, during periods of high current drain on the cells, such as during charge-up of the high voltage capacitors in preparation for delivery of defibrillating shocks.

A pacing section 31 in the therapy generator includes a voltage multiplier and output section (neither of which is shown and both of which are conventional). The multiplier scales up the regulated supply voltage from power source section 28 by multiples of one, two or three. The output section provides output switching from this scaled voltage to deliver pacing stimuli to the patient's heart via the pacing electrodes (not shown), in the manner of a pulse generator, under the control of the microprocessor 10. An analog rate limit circuit 35 controllably limits the pacing rate, to prevent pacemaker runaway in the event of failure of the crystal oscillator circuit 20. The microprocessor 10 automatically disables the rate limiter 35 whenever high rate pacing pulses are required to be delivered, such as for a burst pacing therapy.

The leads (not shown) for the pacing and sensing electrodes (also not shown) are electrically monitored by an isolation/protection circuit 37 to protect low voltage, low power components of the cardiac stimulator from being subjected to the high voltages of the defibrillating shocks generated by the stimulator or applied by an external defibrillator that might be used in the course of emergency medical procedures on the patient.

The cardioverter/defibrillator shock therapy portion of the therapy generator includes an isolated high voltage generator and output section 40, in which an oscillator charges output capacitors to the required level through an isolation transformer, under the control of the microprocessor. A low power analog-to-digital (A/D) converter in section 40 monitors the voltage on the capacitors to assure a microprocessor setting of the desired high voltage output level according to the programmed content of the shock therapy. Monitoring of the capacitor voltage provides the microprocessor with a measure of the residual charge on the capacitors, after delivery of each output pulse, by which to estimate the amount of energy consumed in the delivery for lead impedance measurement. In addition, the A/D converter input circuit may be switched by the microprocessor for connection to the power source section 28 to monitor the battery voltage, and thereby determine the present condition of the cells.

Output section 40 also contains level shifters and isolation transformers (not shown) to convert the microprocessor-supplied low level logic control signals to the control signal levels required to drive the output switches of that section. The switches are of low "on" impedance and capable of handling the high voltages and currents being generated to control the delivery and polarity of each output pulse. A short circuit protection circuit may be employed to open the output circuit in the event that the current therethrough rises above a predetermined level, to prevent destructive capacitor discharge into a very low impedance if, for example, the defibrillator patch electrodes were shorted.

Figure 2:
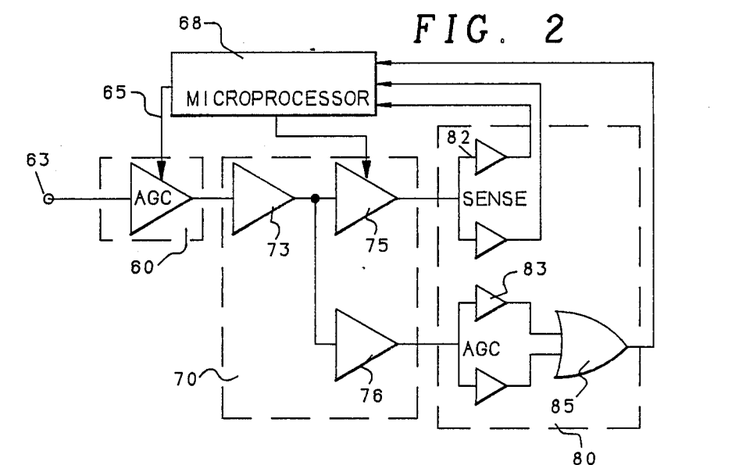
FIG. 2 is a more detailed circuit diagram of the microprocessor and sense amplifier portion of the therapy generator circuit of FIG. 1.

Sense amplifier 25 and its relationship to the microprocessor 10 are illustrated in greater detail in FIG. 2. The ECG waveform components detected by the sensing electrodes (not shown) are applied to an AGC amplifier 60 via an input circuit 63. The gain of amplifier 60 is automatically controlled by a feedback loop 65 containing a portion 68 of the microprocessor/memory section 10 (FIG. 1). The electrogram signals processed by AGC amplifier 60 are further enhanced by a filter section 70 having a primary high gain bandpass amplifier 73 to amplify signals within the band. The output of amplifier 73 is split and applied to separate bandpass amplifiers 75 and 76, the former being digitally controlled by microprocessor portion 68. The output derived from amplifier and filter stages 60 and 70 is applied to a quad comparator 80 (to be described in greater detail below with reference to FIG. 5), comprising a set of sensing target comparators 82 and a set of peak target comparators 83, 85, which develop three inputs to the microprocessor in the feedback loop.

The primary purpose of the inventive system is to track the signals of interest. The sense amplifier with AGC, filter and feedback system of the present invention is implemented to solve the difficult problem of sensing the low frequency, varying amplitude which is characteristic of ventricular fibrillation. It will be recognized that under ordinary circumstances a loss of sensing may be indicative of fibrillation, requiring that the gain of the sense amplifier be increased to enable better detection. If, however, the loss of sensing is attributable, for example, to intermittent heart block rather than to fibrillation, a return of sense signal likely would be over-amplified, with a consequent serious perturbation of the entire system.

The system of FIG. 2 provides dual signal paths or channels having different bandpass characteristics. The signal path through amplifier 75 to the sense comparators 82 determines the sensing point and the signal path through amplifier 76 to the AGC comparators 83 portion is part of the feedback loop that includes the microprocessor 68, which determines the gain of AGC amplifier 60. The sensing margin is defined as the ratio of peak signal size at the inputs to inner comparators 82 and their sensing threshold. A ratio greater than one must be chosen in order to avoid loss of sensing as a consequence of a reduction in signal amplitude. For example, the use of a 2-to-1 margin would mean that the signal amplitude would have to be reduced by one-half to lose sensing. The goal of the AGC system is to maintain a preset sensing margin. For a given threshold level on the sensing comparator, this may be achieved by adjusting the gain of the AGC amplifier so that the peak voltage seen by the sensing comparators remains more or less constant. The microprocessor 68 samples the output of the peak comparators 83 on a cycle by cycle basis. In essence, if the waveform peak exceeds the threshold of the AGC the microprocessor 68 will reduce the gain a small amount. If the waveform peak does not exceed the threshold of the AGC, it will increase the gain a small amount (the increase/decrease decision process will be discussed in more detail later).

The bandpass of the signal path to the sensing comparator is shaped so that frequencies below 25 Hz are attenuated. This gives the desirable effect of attenuating the lower frequency T-wave relative to the QRS complex. However, it has the undesirable effect of attenuating fibrillation signals. But the bandpass of the signal path to the AGC comparator is shaped so that the frequencies in the 3 to 12 HZ range are attenuated even more than they are in the signal path to the sensing comparator. The AGC system will compensate for the attenuation of a fibrillation signal by increasing the gain of the AGC amplifier. However, because the fibrillation signal to the AGC comparator is attenuated more than the signal to the sensing target, after the microprocessor has increased the gain the AGC voltage that appears at the sensing comparator will be higher than the AGC voltage that appears at the sensing comparator when QRS complexes are being sensed. Thus the margin is higher when a fibrillation waveform is present.

With respect to pacing interaction, in the case of a bradycardia patient the gain setting must be appropriate to allow sensing of subsequent fibrillation. Also, the T-wave window must be set to sense T-waves evoked by the pacemaker. In this particular case, the gain is adjusted by the microprocessor so that the T-wave is at approximately the level of the sensing target. The assumptions are that evoked T-waves are larger than intrinsic T-waves, and that the QRS complex is much larger than T-waves. Such a gain is reasonably sufficient to sense fibrillation or a QRS complex.

Figure 3:
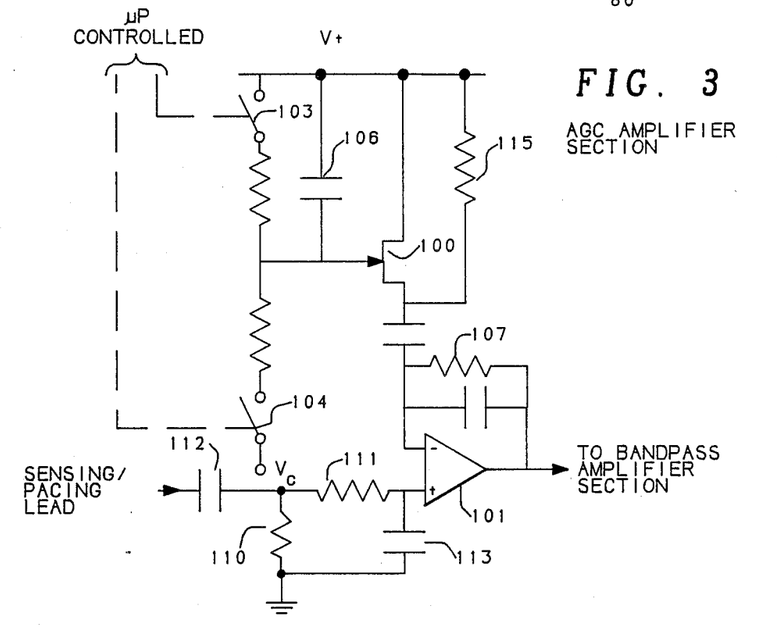
FIG. 3 is a schematic circuit diagram of the AGC amplifier section of the sense amplifier.

Referring to FIG. 3, AGC amplifier 60 of the sense amplifier section 25 provides initial bandpass filtering by means of a circuit consisting of resistors 110 and 111 and capacitors 112 and 113. The AGC amplifier gain is controlled by varying the gate voltage of an N-channel junction field effect transistor (JFET) 100 which acts as a voltage controlled input resistor to a non-inverting amplifier 101. The microprocessor 68 (FIG. 2) controls the on/off duty cycle of switches 103 and 104, to set the gate voltage of JFET 100 by charging and discharging capacitor 106 to a voltage between V+ and $V_c$. This technique is used to obtain a gain range of 30:1 as determined by the resistance of resistor 107 and the on impedance of JFET 100. Resistor 115 allows proper biasing of the JFET circuit. Although switches 103 and 104 are schematically depicted as mechanical devices in the AGC amplifier circuit of FIG. 3 and in some of the other circuit diagrams, it will be understood that in practice electronic switches (such as field effect transistors) typically would be employed.

Figure 4:
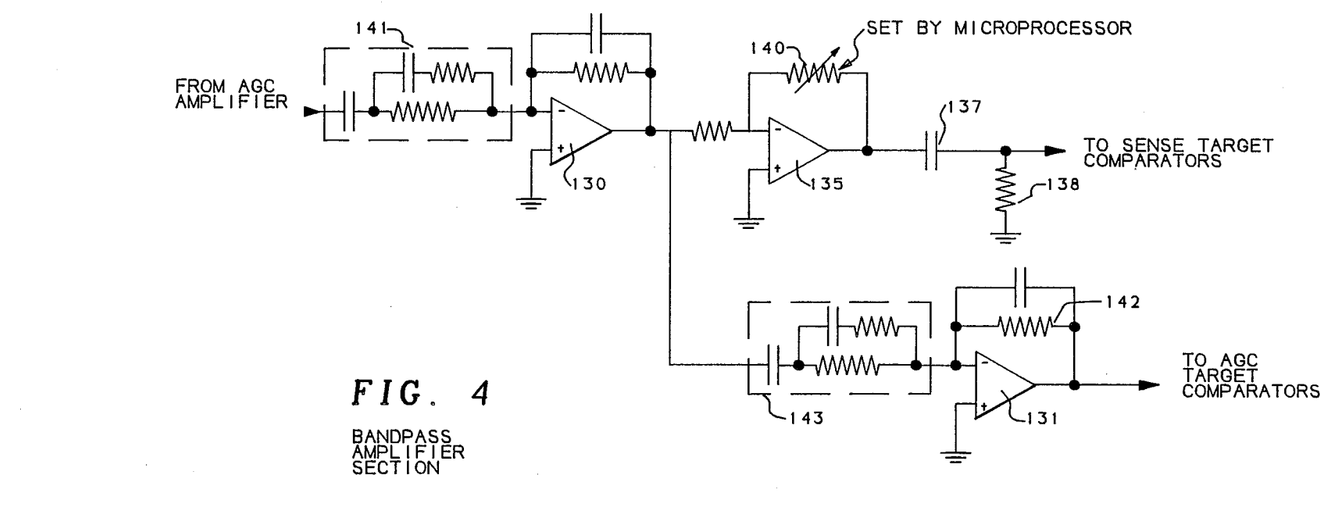
FIG. 4 is a schematic circuit diagram of the bandpass amplifier section of the sense amplifier.

Turning now FIG. 4, the output of the AGC amplifier section 60 is supplied to bandpass amplifier section 70 of sense amplifier 25. Section 70 has a programmable sensing margin feature and special bandpass characteristics which aid in tracking the variable amplitude fibrillation signal. The overall bandpass amplifier includes two active bandpass filter amplifiers 130 and 131, a programmable gain DC amplifier 135, and a passive high pass filter comprising capacitor 137 and resistor 138. This circuit reduces the amplitude of the signal components outside the frequency band of interest, and increases the sensing margin for the low frequency fibrillation signals. The microprocessor 68 sets the magnitude of resistance 140, and therefore can set the gain of DC amplifier 135 and, thus, the gain to the sensing target comparators separately from the gain to the AGC target comparators. In this manner, the sensing margin (which is proportional to the ratio between the sensing and AGC targets) is programmable, being selectable by the microprocessor. Alternatively, the effective ratio of the targets ( and, therefore, the sensing margin) could be programmably changed by varying the gain of bandpass filter amplifier 131 through changes of the value of resistor 142, or by changing the target reference voltages themselves.

Figure 5:
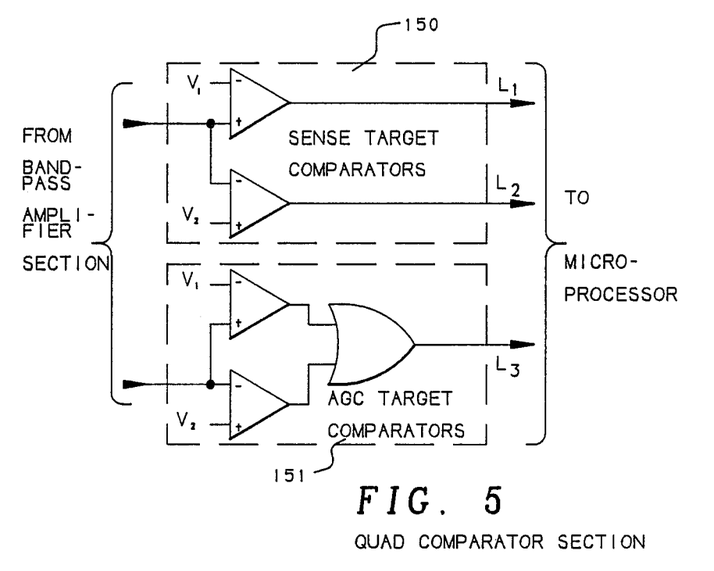
FIG. 5 is a schematic circuit diagram of the quad comparator section of the sense amplifier.
Figure 6:
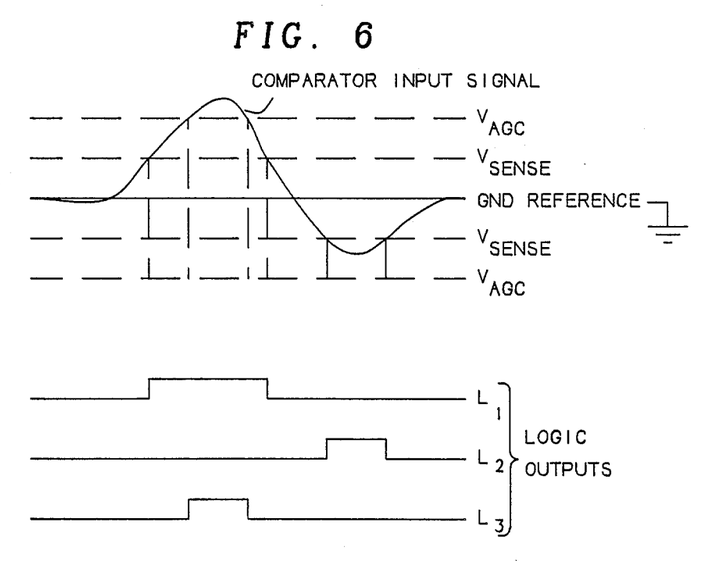
FIGS. 6 through 9 are waveforms useful for describing the operation of the sense amplifier according to the presently preferred embodiment.

The quad comparator 80 of sense amplifier 25 is shown in FIG. 5, and an exemplary input signal and logic outputs of the comparator are illustrated in FIG. 6. The comparator has two comparator pairs comprising sensing target comparators 150 and AGC target comparators 151. The logic outputs $L_1$ and $L_2$ (upper and lower, respectively) of the sensing target comparators are used by the microprocessor as valid sense input signals. The logical "OR" ($L_3$, either positive or negative) of the AGC target comparators is used by the microprocessor to evaluate the need for increasing or decreasing the AGC amplifier gain. The sensing targets represent a sensing threshold, and the AGC targets represent a sensed signal peak amplitude target.

Figure 7:
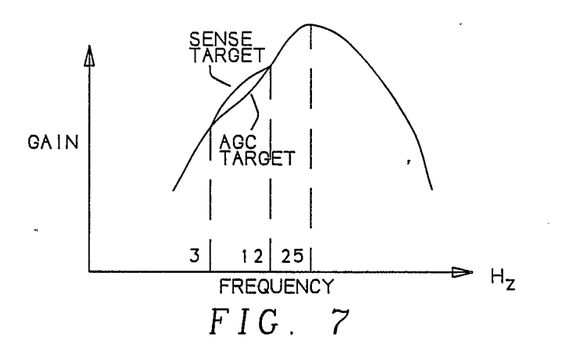

During sinus rhythm, the amplitude of the QRS complex dictates the gain setting of the AGC amplifier because of the relatively large amplitude and high frequency content of the QRS. The same situation exists during sensing of a tachycardia. However, in the presence of a lower frequency fibrillation signal there is nearly a doubling of the sensing margin, because of the bandpass filters 141 and 143 (FIG. 4), thereby permitting more reliable tracking of the variable amplitude fibrillation signal. In this respect, it will be recognized that the series resistance-capacitance path in parallel with the resistance path of each of circuits 141 and 143 provides an input impedance to the respective operational amplifiers 130 and 131 such that the gain at high frequencies will be more than the gain at low frequencies. Thus, the frequency plot for the input signal to the AGC targets constitutes a bandpass (FIG. 7) which will pass QRS complexes faithfully, while T-waves will be relatively attenuated to minimize double sensing. Fibrillation signals will be passed accurately, although relatively attenuated, but will boost the gain of the AGC to over-compensate.

Figure 8:
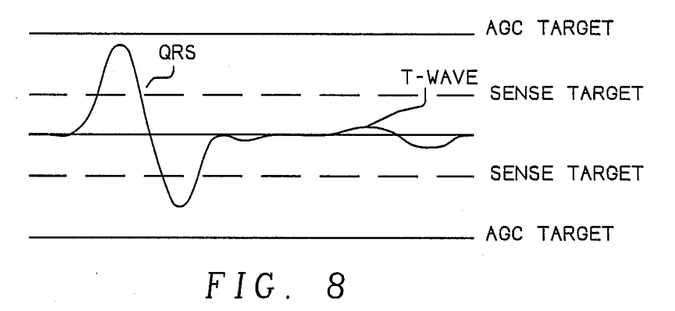

By way of an example of operation, in the presence of a QRS complex which is being monitored by the sense amplifier with its sensing and AGC targets, the microprocessor 68 seeks to maintain the gain in such a way that the peak of the signal in the QRS complex approximately crosses the AGC target, as shown in FIG. 8. Such gain maintenance is achieved in the following manner. Any signal that crosses the sensing targets is considered to be a sense event. If a sense event occurs in a cardiac cycle, then sometime after it is sensed (which may, for example, occur during the refractory period, although the precise time is not significant) a flag is checked which indicates whether or not the AGC target was crossed by that sense event. If the AGC target was crossed, it is an indication that the gain is too high and should be decreased. At that point, the microprocessor decreases the gain. In the presently preferred embodiment, the gain is decreased by a certain percentage. As an alternative, however, the gain may be decreased by a fixed amount.

The microprocessor also counts cycles in which sense events have occurred but there has been no crossing of the AGC target. If two consecutive cycles are detected in which the sensing target is crossed but the AGC target is not, the microprocessor recognizes that the gain is too low and must be increased. Here again, the increase may be effected as a fixed percentage or a fixed amount.

If a fixed amplitude QRS complex is detected, a repeated pattern of alternately increasing and decreasing the sense amplifier gain takes place, controlled by the microprocessor in the previously described manner. When the gain is increased, the signal crosses the AGC target. The gain is then decreased, is maintained low for two cycles, and is then increased again, all as consequence of the fixed amplitude of the incoming signal and the operation of the AGC, filter and comparator circuits in conjunction with the microprocessor. This process is referred to as "dithering" in which the peak amplitude is dithered around the threshold of the AGC comparator in the presence of normal sensed activity. In essence, the amplitude of the sensed amplified signal is increased and decreased by small amounts in such a way that the peak of the signal is approximately at the level of the AGC target.

Dither flags are "set" or cleared at various times during the performance of the AGC decision process. Two flags are utilized, one of which is set when a detected event crosses the AGC target and changes the gain, and the other of which is set when two consecutive sensed events fail to cross the AGC target. These are referred to as "dither up" and "dither down," respectively. If, for example, the patient is in fibrillation, the detected signal is very small and the gain of the sense amplifier is very high. After delivery of shock therapy and consequent defibrillation, the detected cardiac signal now appears to be very large because the gain of the amplifier is no longer appropriate. The desire is to avoid rate counting any target crossings to determine whether an arrythmia is present until the gain has been restored to an appropriate level. A determination is made that the gain is appropriate when the dither flags are "set," which may, for example, take place when the gain is increased. At that point, the detection system is locked into the signal. Upon setting of both bits the dither criterion is achieved, and valid tachycardia detection or fibrillation detection may then validly proceed. The situation, and the need to reestablish the appropriate gain, will change only after a pace event or after an anti-tachycardia therapy.

Figure 9:
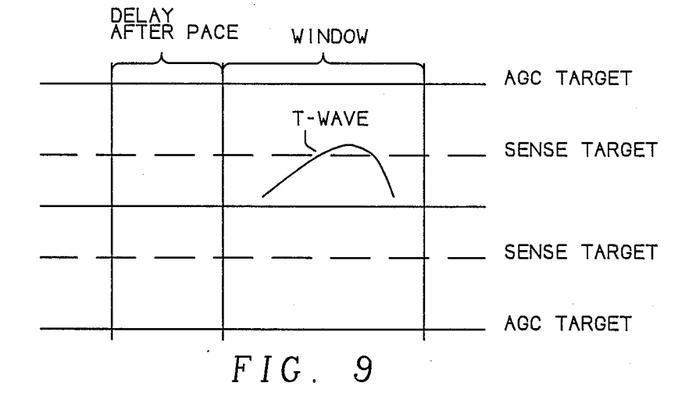

Consideration must be given to the manner in which the gain is to be adjusted during bradycardia pacing, where, for example, a lack of sensed events may be attributable to either a slow heart rate or an inadequate gain setting of the sense amplifier. To determine which of these is responsible, sensing of the relatively lower frequency post-pace T-waves is performed. If no T-wave is sensed at the sensing target comparators in a preset time window following a pace event, the AGC gain is increased. This is continued until the amplitude of a T-wave exceeds the sensing target and is thereby sensed, as indicated in FIG. 9, or until the previously undetected heart rhythm is sensed. The major differences between the gain control based on post-pace T-waves and the gain control based on QRS and fibrillation signals are the time window and that the T-wave amplitudes are controlled about the sensing target rather than the AGC target. This tends to assure that the amplifier gain is not set too high in the event that an intrinsic QRS signal is sensed; that is, to avoid double sensing of QRS followed by a T-wave.

In the case of bradycardia, then, the sense amplifier will see pace events instead of a QRS complex. If capture is achieved, a T-wave will follow each pace event. It is known that T-waves are of lower amplitude than QRS complexes, and that post-paced T-waves are of greater amplitude than intrinsic T-waves. The invention takes advantage of these characteristics in that the window indicated in FIG. 9 is opened a predetermined delay interval after a pace—for example, an interval of 200 to 400 milliseconds after the pace—and a T-wave is looked for during the window period. If a T-wave is sensed, the gain is adjusted by microprocessor control to dither the amplitude of that wave around the sensing target, as shown in FIG. 9, in a manner corresponding to that previously described for dithering about the AGC target.

The assumption is made that after a pace event the patient's heart may be in fibrillation or bradycardia (or the gain may be too low). If the gain is set to just barely sense something in the window period, and fibrillation is present, there generally will be signals which occur after the T-wave window and before the next pace. In that case, it is recognized that the next cycle will not be a pace cycle, and there is no need to look for a T-wave. A different algorithm is followed to reduce the time required to detect defibrillation in these circumstances. If, after two consecutive paces nothing is sensed in the T-wave interval, the gain is increased by a relatively large amount (i.e., the sensitivity of the sense amplifier is considerably increased) in an attempt to detect a fibrillation signal. The process is repeated if, after increasing the gain, there is still no detection of a T-wave or fibrillation following two consecutive paces. In this way, the gain undergoes rapid change to seek some kind of signal. The programmable maximum gain is nominally the maximum gain of the device. In the presently preferred embodiment, maximum gain can be programmed such that the device is sufficiently sensitive to detect signals as low as 0.3 to 0.5 millivolts.

For bradycardia pacing, the AGC and sense targets are set at two-to-one because the area of interest is the relationship between the QRS and the T-wave. However, in situations where one morphology of waveform may be present for a while and an abrupt shift may take place to another morphology, a greater sense margin is required.

With the above considerations in mind, the following AGC algorithms are implemented in the presently preferred embodiment of the invention:

1. Reduce gain by a small amount after one high gain sense event. Increase gain by a small amount after two sequential low gain sense events, and each subsequent low gain sense event.

The rationale for an initial ratio of two low gain sense events to increase gain to one high gain event to decrease gain is that, in so doing, the very high R-waves are allowed to dominate the AGC adjustment until the R-waves are dithering about the AGC target. In that case, if the sense margin is correctly set, T-waves should not be sensed. Equivalently, the margin must be set so that an R-wave and its T-wave cannot both be sensed as low gain events. However, the requirement of two sequential low gain sense events makes the gain increase portion of this algorithm somewhat erratic in the presence of fibrillation, because of the possibility that a run of two sequential low gain sense events may not be found in fibrillation. For example, the sequence might be high gain/low gain/no-sense, followed by a bradycardia pace.

2. For a bradycardia pace event: (a) if a T-wave crossed the AGC target (in the T-wave window), decrease the gain by a small amount; (b) if a T-wave crossed the sensing target but not the AGC target, and there has been a step increase in gain but there has not yet been an R-wave sense event, decrease the gain by a small amount; (c) if a T-wave has not crossed the sensing target, increase the gain by twice the "small decrease" amount; (d) if there are two sequential brady pace/no T-wave events, increase the gain by a large step and clear the dither flags, and step increase the gain again on each following consecutive brady pace/no T-wave event.

A T-wave may not be sensed after a brady pace event for any of the following reasons: (i) the T-wave did not exceed the sensing target, (ii) the pacing took place during fibrillation, (iii) a fusion beat was followed by an abnormal T-wave, (iv) there was a failure to capture, or (v) there was a failure of the sensing system.

3. If brady pacing causes a step increase in gain, clear the dither flags. Double the incremental step size used to increase and decrease the gain on R-wave events until the gain dithers.

The rationale here comes from dog studies in which fusion beats were found to produce waveforms with abnormally small post-pace T-waves, thereby causing step increases in gain which, in turn, resulted in serious over-amplification. Therefore, in the presently preferred embodiment, the dither flags are cleared after a step increase in gain, and rhythm classification is not resumed until the gain has dithered which will not occur until any over-amplification has been corrected. Because this tends to increase fibrillation detection time, which is contrary to the reason for the step increase in gain, the incremental step size is doubled when the dither flags are cleared. Thereby, the search time is decreased without leading to significant under- or over-sensing.

4. After an anti-arrhythmic therapy, clear the dither flags. In all cases, do not attempt to classify the cardiac rhythm until the gain has increased (i.e., as a result of two sequential low gain events).

The rationale here is that rhythm classification probably should not begin until the gain is locked on the event but, since this can inordinately lengthen the time for detection of fibrillation, a reasonable compromise is to commence classification as soon as it can be ascertained that the system is not over-amplified, which is after two consecutive low sense events.

5. If gain is driven to the maximum by R-wave sensing and the R-wave has not yet crossed the AGC target, set the dither flags. If gain is driven to the minimum by any sequence of events, set the dither flags.

6. If noise is sensed during quiet time, and the noise crossed the AGC target, reduce the gain by a small amount. If the noise does not cross the AGC target, do not adjust the gain.

7. If a programmable number of consecutive gain decreases occur, then inhibit rhythm classification until a gain increase occurs. This reduces the likelihood of inappropriate detection due to over-amplification of rhythms which change spontaneously or due to external influences (e.g. cardioversion).

Although a presently preferred embodiment of the invention has been described herein, it will be apparent to those skilled in the field to which the invention pertains that the variations and modifications of the disclosed embodiment may be implemented without departing from the true spirit and scope of the invention. Accordingly, it is intended that the invention shall be limited only to the extent required by the appended claims and the relevant principles of the applicable law.

What is claimed is:

1. Apparatus for detecting cardiac arrhythmias by analyzing ECG signals produced by the heart, comprising:
    filter means forming dual signal paths having different bandpass characteristics for receiving said ECG signals, one of said signal paths constituting means for determining a sensing level for the ECG signals, and the other of the signal paths constituting feedback loop means for determining ECG signal gain and a sensing margin which is a function of the frequency content of the ECG signal.

2. The invention according to claim 1, further comprising:
    a microprocessor in said feedback loop means.

3. The invention according to claim 1, further comprising:
    means in said feedback loop maintaining a user selectable sensing margin.

4. The invention according to claim 1, in which said feedback loop means includes means for maintaining said sensing margin at a ratio of peak signal amplitude-to-sensing threshold level of at least 2-to-1.

5. The invention according to claim 4, further including:
    means in said feedback loop means for programming said sensing margin.

6. The invention according to claim 1, in which said filter means forming dual signal paths includes means for adjusting bandpass characteristics of each said paths such that low frequencies are de-emphasized in the path that determines signal gain and sensing margin.

7. Implantable apparatus for detecting cardiac arrhythmias, comprising:
    electrode means for sensing electrical activity of a patient's heart, and
    processing means responsive to the sensed electrical activity for determining whether sensed events are indicative of arrhythmias, said processing means including target means establishing at least one reference level against which the amplitudes of predetermined sensed events are compared, gain control means controllably varying sensitivity of the processing means according to the amplitude of each sensed event relative to said at least one reference level, and comparison means responsive to said gain control means being adjusted in sensitivity in one direction immediately following an adjustment in the other direction for counting the number of times the sensed event crosses the reference level as an indication of the nature of the arrhythmia.

8. The invention according to claim 7, further comprising:
    means responsive to said processing means determining presence of an arrhythmia for delivering a therapy to the heart specifically for the treatment of that arrhythmia to restore normal sinus rhythm.

9. An implantable stimulator for detecting and treating cardiac arrhythmias, comprising:
    sensing means responsive to electrical activity of a heart and adapted to produce electrical signals representative of electrical activity of the heart, and
    signal processing means forming dual signal paths with different bandpass characteristics and responsive to the electrical signals for programmably controlling the sensing margin of the stimulator to components of said signals indicative of arrhythmia.

10. The implantable stimulator of claim 9, wherein said signal processing means comprises:
    amplifier means adapted to variably adjust the amplification of the electrical signals whereby detection of arrhythmias is enhanced.

11. The implantable stimulator of claim 10, wherein said signal processing means further comprises:
    a feedback loop for said amplifier means; and
    microprocessor means in said feedback loop adapted to control said amplifier means according to preselected algorithms.

12. The implantable stimulator of claim 11, wherein aid signal processing means further comprises:
    means for filtering said electrical signals passing only those signals in a predetermined frequency band.

13. Method of detecting cardiac arrhythmias, comprising the steps of:
providing means for detecting electrical activity of a heart including both sinus rhythm and arrhythmias and producing electrical signals representative of that activity; and
processing the electrical signals along dual signal paths having different bandpass characteristics while variably controlling sensitivity in response to selected components of said signals whereby detection of arrhythmias of interest is enhanced.

14. An implantable defibrillator for automatically treating cardiac abnormalities, comprising:
means for detecting electrical activity representing cardiac abnormalities of a heart; and
means defining dual signal paths having different bandpass characteristics and responsive to the detected electrical activity for enhancing the frequency characteristics thereof and the amplitude of preselected frequency content indicative of designated cardiac abnormalities relative to predetermined threshold levels, to distinguish various abnormalities from one another including fibrillation, bradycardia, and tachycardia, to treat said abnormality.

15. An implantable cardiac stimulator for detecting cardiac arrhythmias, comprising:
means for sensing cardiac signals;
amplifier means responsive to sensed cardiac signals for detecting and distinguishing normal and abnormal cardiac activity therefrom, said amplifier means including;
means defining dual signal paths for processing portions of the sensed signals representative of cardiac activity in two frequency bands each having different bandpass characteristics, and
means in one of said signal paths for automatically adjusting the gain of the amplifier means according to the amplitude of the signals in one said frequency band to detect abnormal cardiac activity therefrom.

16. The implantable cardiac stimulator of claim 15, further comprising:
means responsive to abnormal cardiac activity for delivering a therapy appropriate to restore normal cardiac activity.

17. The implantable cardiac stimulator of claim 15, wherein said gain adjusting means comprises:
means defining a feedback loop for said amplifier means, and microprocessor means in said feedback loop varying the gain of the amplifier means according to at least one predetermined algorithm selected to enhance the detection of a particular episode of abnormal cardiac activity.

18. The method of claim 13, wherein detection of two low signals in a row causes an increase in gain.

19. The method of claim 13, wherein detection of one high signal causes a decrease in gain.

20. The implantable cardiac stimulator of claim 15, wherein said amplifier means detects cardiac arrhythmias in the sensed cardiac signals.

21. The implantable cardiac stimulator of claim 20, wherein said amplifier means is adapted to distinguish bradycardia, tachycardia and fibrillation among the cardiac arrhythmias detected from the sensed cardiac signals.

22. The implantable cardiac stimulator of claim 15, wherein said amplifier means further comprises:
means for establishing a sensing margin for the amplifier means as a ratio of peak signal amplitude to sensing threshold.

23. The implantable cardiac stimulator of claim 22, further comprising:
means for programming said sensing margin.

24. An implantable cardiac stimulator for detecting cardiac arrhythmias by analyzing electrical signals produced by the heart, comprising:
means for detecting electrical signals produced by the heart; and
amplifier means responsive to the detected signals and having dual signal paths for said detected signals, each said signal path having different bandpass characteristics, means defining a feedback loop in one of said paths for automatically adjusting the gain of the amplifier means whereby gain and threshold relationships between said dual signal paths are controlled to produce variable sensing margins for different input waveforms.

25. An implantable cardiac stimulator according to claim 24, wherein an algorithm controlling gain requires sensing of two lows in a row to increase gain.

26. An implantable cardiac stimulator according to claim 24, wherein an algorithm controlling gain requires sensing one high to decrease gain.

27. An implantable cardiac stimulator according to claim 24, wherein an algorithm controlling gain requires a ratio of greater than 1 to 1 to avoid T-wave sensing.

28. An implantable cardiac stimulator according to claim 27, wherein said ratio is 2:1.

29. An implantable cardiac stimulator according to claim 24, wherein an algorithm controlling gain avoids over-amplification when no valid signal is present, for purpose of noise immunity, and appropriate sensing when signals return.

30. An implantable cardiac stimulator according to claim 24, wherein an algorithm controls gain to optimize gain tracking responsiveness.

31. An implantable cardiac stimulator according to claim 24, wherein an algorithm controls gain to interact with arrhythmia detection.

32. An implantable defibrillator for automatically treating cardiac abnormalities, comprising:
means for detecting electrical signals of a heart and distinguishing electrical signals representing cardiac abnormalities; and
dual signal path means receiving said detected signals, each said path means having a different bandpass characteristic one said signal path means determining a sensing level for said signals and the other signal path having feedback loop means controlling gain thereby producing different sensing margins for different input electrical signal waveforms.

33. An implantable defibrillator according to claim 32, wherein a high level margin is produced to detect erratic fibrillation signals.

34. An implantable defibrillator according to claim 32, wherein a low level margin is produced to detect QRS complexes while avoiding sensing of T-waves.

* * * * *